United States Patent [19]

Sihvonen

[11] Patent Number: 5,755,675
[45] Date of Patent: May 26, 1998

[54] METHOD FOR MEASURING THE FUNCTION OF JOINTS AND ASSOCIATED MUSCLES

[76] Inventor: Teuvo Sihvonen, Lampaankuja 10, FIN-70780 Kuopio, Finland

[21] Appl. No.: 406,851

[22] PCT Filed: Oct. 1, 1993

[86] PCT No.: PCT/FI93/00392

§ 371 Date: Jul. 17, 1995

§ 102(e) Date: Jul. 17, 1995

[87] PCT Pub. No.: WO94/07414

PCT Pub. Date: Apr. 14, 1994

[30] Foreign Application Priority Data

Oct. 2, 1992 [FI] Finland ................................ 924455

[51] Int. Cl.[6] ........................................................... A61B 5/00
[52] U.S. Cl. .................................................................. 600/594
[58] Field of Search ........................................ 128/733, 774, 128/781, 782

[56] References Cited

U.S. PATENT DOCUMENTS

| | | | |
|---|---|---|---|
| 4,108,164 | 8/1978 | Hall | 128/781 |
| 4,655,227 | 4/1987 | Gracovetsky | 128/781 |
| 4,664,130 | 5/1987 | Gracovetsky | 128/781 |
| 4,699,156 | 10/1987 | Gracovetsky | 128/781 |
| 4,971,069 | 11/1990 | Gracovetsky | 128/781 |
| 5,085,226 | 2/1992 | DeLuca et al. | 128/733 |
| 5,163,440 | 11/1992 | DeLuca et al. | 128/733 |
| 5,361,775 | 11/1994 | Remes et al. | 128/781 |

OTHER PUBLICATIONS

Pain, 8 (1980) pages 1–10; Chronic Back Pain; Steven F. Brena et al.

1986 Volvo Award in Biomechanics; Partitioning of the L4–L5 Dynamic Moment into Disc, Ligamentous, and Muscular Components During Lifting; S. M. McGill et al; pp. 666–679; 1986.

Spine; vol. 15, No. 3; 1990; pp. 250–253.

American Journal of Physical Medicine; Normative Data on Low Back Mobility and Activity Levels[1]; vol. 58, No. 5.; pp. 217–229; 1979.

J. Biomechanics, vol. 19, No. 8, pp. 565–577, 1986. Effect of Muscular Activity on Valugs/Varus Laxity and Stiffness of the Knee; T. G. Olmstead, et al.

An Electromyographic Study of Elbow Motion During Postexercise Muscle Sorenes; John H. Howell et al.; pp. 1713–1719; 1985.

Pain; vol. 34 (1988) pp. 153–160; Comparison of Lumbar Paravertebral EMG Patterns in Chronic Low Back Pain Patients and Non–Patient Controls; David K. Ahern et al.

Experimental Brain Research; vol. 88 (1992) pp. 41–58; Electromyographic Studies of Neck Muscles in the Intact Cat; F.J. R. Richmond et al.

*Primary Examiner*—Max Hindenburg
*Attorney, Agent, or Firm*—Burns, Doane Swecker & Mathis, LLP

[57] ABSTRACT

The invention relates to a method for measuring the function of joints and associated muscles. The method comprises measuring, on the one hand, the mobility of a person in a desired area and, on the other hand, simultaneously by means of electromyography (EMG) measuring the electrical activity of muscles in the same area, and evaluating the abnormality in the mobility and in the function of the muscles of said area, caused especially by pain, by comparing the measured values with reference values compiled in advance.

17 Claims, 2 Drawing Sheets

METHOD FOR MEASURING THE FUNCTION OF JOINTS AND ASSOCIATED MUSCLES

BACKGROUND OF THE INVENTION

The invention relates to a method for measuring the function of joints and associated muscles.

The causes of various joint disorders are mainly unknown, and it is often impossible to detect them objectively. It seems, for example, that back pain of even short duration leads to a decline in the muscular activity, functional disorders of the back, and restrictions of motion. The aim of treatment is usually to restore declined muscle function and improve the functional protection and mobility of the back, and thereby to reduce mechanical load and pain-giving stimuli.

When evaluating the change in the functional state and the degree of disability in connection with examination and treatment of patients suffering from joint disorders, a doctor must largely draw on the visual impression that he gets. Doctors have always tried to analyze functional disability subjectively by evaluating, for instance, the effortlessness of movements of the back, and muscular reactions. They have tried to get an impression of the functional state by evaluating the mobility and the maximum muscle forces. There have also been attempts to correlate back pain with changes in the spinal structure and the ranges of motion determined in extreme positions. Recently the maximum forces of body torsions have been measured to provide support for treatment.

For the reasons stated above, it is not quite simple to take reliable measurements of a person in pain. In addition, these measurements do not provide information on the ease of normal functions or on the mobility of the back as a continuous series of functions; it is possible to measure only the extreme positions.

Previously it has thus been impossible to measure the interactions between motion and muscular activity and the changes in them, for example, in connection with back disorders such as sciatica. So far it has been almost impossible to measure the third decisive functional factor in addition to total mobility and muscular strength, i.e. the motor skill or coordinative ability.

OBJECTS AND SUMMARY

An object of the present invention is to provide a method for measuring the movements of joints and muscles, by means of which method the above-mentioned disadvantages can be largely eliminated, and to provide a system in which the functions performed during movements can be converted into unambiguous curves and numbers. The method of the invention is characterized by measuring, on the one hand, the mobility of a person in a desired area and, on the other hand, simultaneously by means of electromyography (EMG) the electrical activity of muscles in the same area, and evaluating the abnormality in the mobility and in the function of the muscles in said area, caused especially by pain, by comparing the measured values with reference values compiled in advance.

By the method of the invention, the functions performed during a movement of the back can be converted into data which can be unambiguously processed, in contrast with an impression obtained merely by observing and/or verbal description. By the method according to the invention it is possible to simultaneously monitor the variation in muscle contraction, and the different factors of the motion of the back, their number, velocity and degree of muscular activity, and their timing with respect to motion. It has turned out that there are significant differences in these factors between healthy people and those suffering from back disorders, and the degree of these differences can be determined by measuring. A functional disorder depends on the intensity of pain signals and alarm mechanisms of tissues and on the changes in mobility. The measuring data obtained by means of the invention can be used for describing the condition of a patient and as a supplement to examination data obtained by other methods when decisions concerning treatment and/or, for example, insurance are made. In addition, the method of the invention can be used to monitor and measure the effect of treatment. The method according to the invention is not, however, a diagnostic method but a way of collecting data for diagnosis. It is a doctor who is responsible for making diagnosis and giving treatment. The doctor makes his decision on the basis of several different methods of observation, which always include feeling and interviewing the patient, and which do not form a part of the present invention.

BRIEF DESCRIPTION OF THE DRAWINGS

In the following, the invention will be described in greater detail with reference to the accompanying drawings, in which.

DETAILED DESCRIPTION OF PREFERRED EMBODIMENTS

Figures 1A, 1B, 1C:
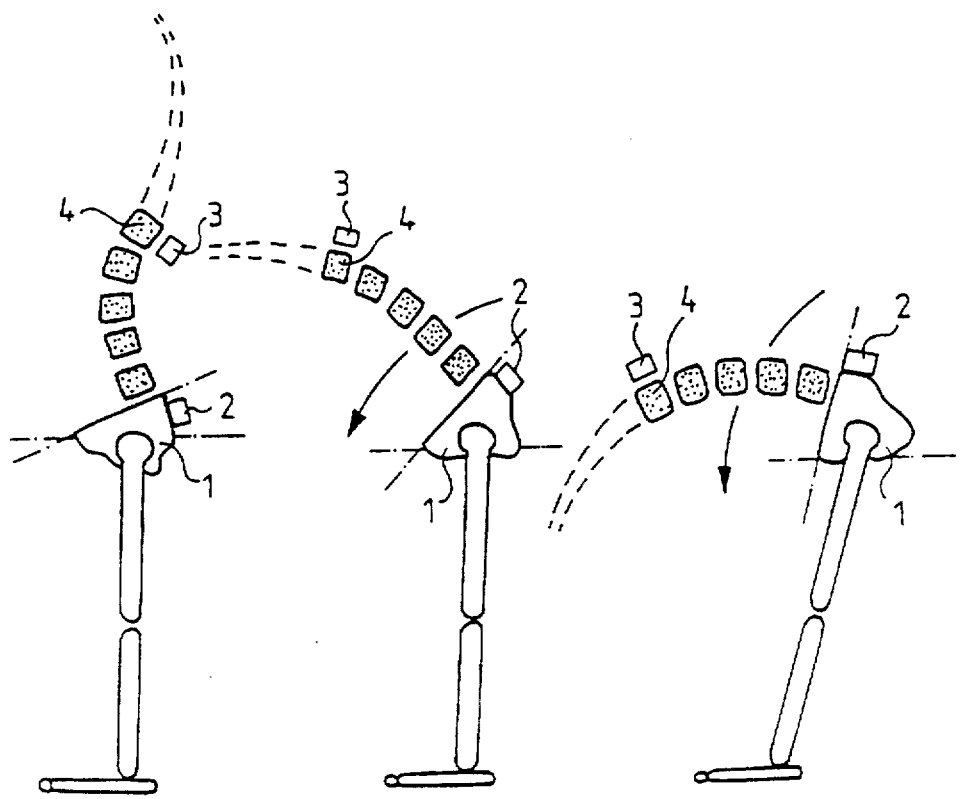
FIGS. 1A through 1C illustrate sensors measuring motions of the back in accordance with the invention.

FIG. 1 shows a sensor 2 (e.g. an angle sensor) for continuously registering the movements of the sacrum 1, said sensor being fixed, for instance, by a tape at the sacrum. Accordingly, another continuously operating sensor 3, which may be a motion sensor or an acceleration sensor, is fixed onto a desired part 4 of the back, in this case on the upper part of the lumbar spine. The sensor 3 measures the total motion of its fixing point 4 in the area of the upper body. If the motion measured by the sacrum sensor 2 is subtracted from that measured by the sensor 3, it is possible to get information on the mechanical functioning of the spine as a continuous process between different postures (a–c) in the area between the sensors, in this case in the area of the lumbar spine.

Figures 2A, 2B:
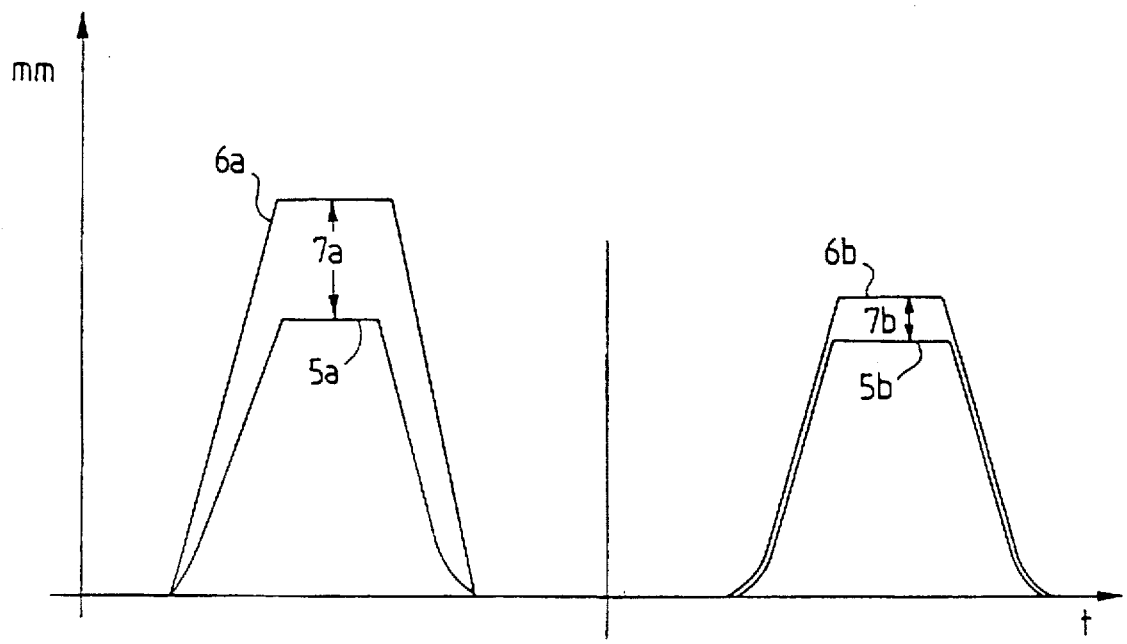
FIGS. 2A and 2B illustrate the mobility of the back in the case of a healthy person and a person suffering from a back disorder.

FIG. 2 shows diagrams obtained by a device developed for the method according to the invention. Diagram A on the left illustrates the mobility of the back of a healthy person, and diagram B on the right illustrates that of the back of a person suffering from a back disorder. The horizontal axis is a time axis, and the vertical axis shows the extension of motion. As illustrated in FIG. 1, the flexion and extension cycle of the back is monitored in this case in the area of the lumbar spine by measuring the motion simultaneously both in the sacral area (curves 5a and 5b) and on the upper portion of the lumbar spine (curves 6a and 6b). The difference 7a, 7b between these motions represents the bend of the lumbar spine (degree of stretch if a stretch sensor is used) as compared with the normal position, i.e. the erect posture; it is also possible to determine the velocity of motions in the areas desired.

Figures 3A, 3B:
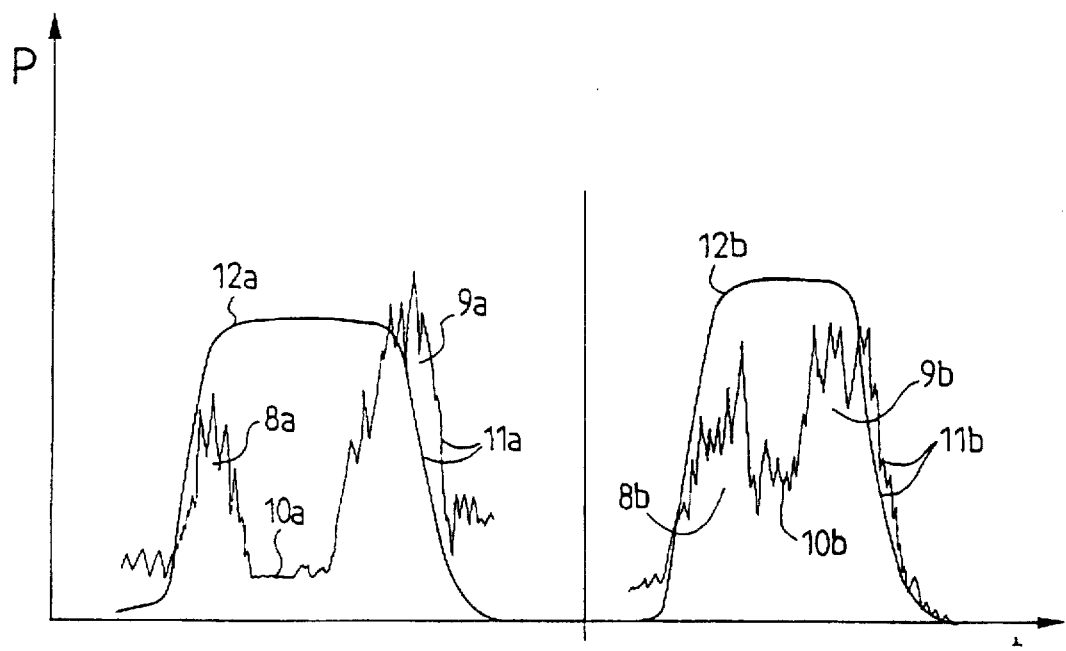
FIGS. 3A and 3B show rectified EMG curves in the case of a healthy person and a person suffering from a back disorder.

At the same time as the mobility of the back is measured in accordance with FIGS. 1 and 2, the muscular activity of the lumbar spine is measured, according to the invention, in a manner known per se by means of electromyography (EMG). In practice this is performed by fixing ECG sensors 13 or corresponding sensors measuring weak electric currents onto a patient's skin, on top of muscles. FIG. 3 (parts A and B as in FIG. 2) illustrates the electrical activity of muscles during a flexion and extension cycle in the form of rectified envelopes of registered EMG signals, i.e. electromyographs. The horizontal axis represents time, and the vertical axis the strength of the EMG signals. In the case of a healthy person, it can be seen that there are muscle contractions 8a and 9a during both the flexion and the extension, and a distinct relaxation phase 10a between them. These diagrams also include curves 12a and 12b, which the device has drawn, and which correspond to FIG. 2 and illustrate the total mobility of the lumbar spine; the timing of these curves can thus be compared with the muscle contractions, e.g. at the points 11a and 11b. One of the embodiments of the invention comprises a step where the flexion values of the back and the corresponding electric muscle signals are mutually comparable with respect to timing.

Figure 4A:
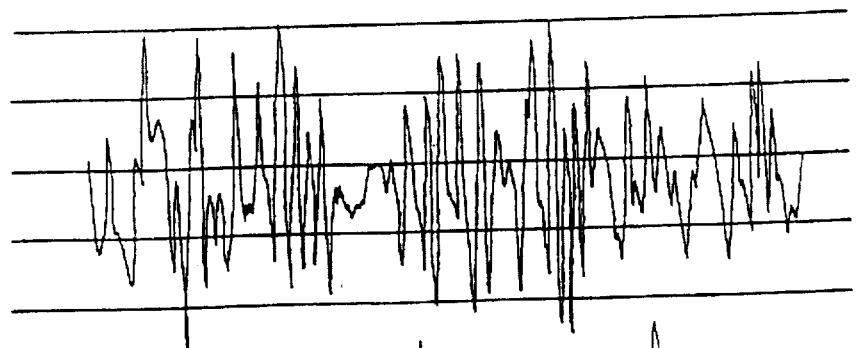
FIGS. 4A and 4B show the curves of rough EMG signals corresponding to FIG. 3.
Figure 4B:
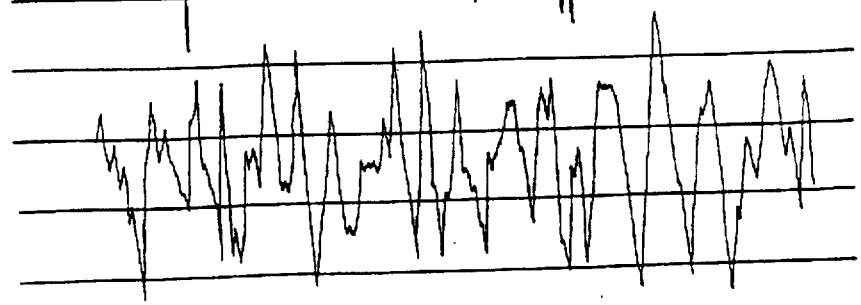

It can be seen that the curves of a healthy person differ clearly from those of a person with pain in the low back area with respect to the EMG signal generated by muscle contractions (8b and 9b), the length and level of the relaxation phase 10b, and the timing (11b) of contractions as compared with the motion. Further information on the muscular activity can be obtained by examining the rough EMG signals as such on a time-amplitude axis (FIG. 4). Changes in the functional state and fatigability of the muscle cells can be accurately indicated by determining the frequency spectrum of the signals (e.g. by a fast Fourier transformation FFT). The use of several measuring channels renders it possible to compare the functioning of different parts of a back muscle. The signal A of FIG. 4 is measured from a healthy muscle which is readily activated, and the signal B is measured from a muscle with functional disorder due to back pain. It can be seen that although both of the signals may have the same amplitude, the differences in the frequency spectrum of the signals are evident: there is clearly a greater number of healthy, active muscle cells having an effect of the EMG signal. Within the scope of the method according to the invention it is also possible to determine the fatigability of an active muscle on the basis of changes in the frequency spectrum of an electric muscle signal.

The method according to the invention renders it thus possible, by drawing and examining the above-mentioned curves, to correlate the measuring results with each other and with the observations made of the patient. The invention provides thus a reliable method of collecting data for a method of diagnosing and monitoring cases of muscular pain. The method according to the invention and the equipment developed to carry out this method are suitable for use as a matter of routine in institutions where back pain patients are examined and treated. The performance of the method and the interpretation of the measuring results can be expedited and facilitated by means of a computer which automatically interprets the values and curves measured and correlates them with the corresponding normal values. The various curves can be printed out as such, arranged in tabular form, or drawn over a normal diagram.

In the same way as in an expert system, the curves may be provided with verbal comments on the basis of the deviations measured. Such a system can be extended to measure and observe even other signals, and it can be used to combine the results of different measurements to form desired reference results, e.g. with respect to the timing, frequency or amplitude of measuring signals, etc.

It will be clear to one skilled in the art that the various embodiments of the invention are not restricted to the examples described above but may vary freely within the scope of the appended claims. The invention is thus applicable for monitoring the muscular activity and motion at any part of the body and even in animals, wherever it is possible and expedient to perform the necessary measurements.

I claim:

1. A method of measuring the function of joints and associated muscles, comprising the steps of:

measuring the mobility of a person in a desired area, simultaneously measuring by means of electromyography (EMG) the electrical activity of muscles in the desired area, evaluating any abnormality in the mobility and in the function of the muscles in the desired area, caused especially by pain, by comparing the measured values with reference values compiled in advance; and determining the fatigability of an active muscle on the basis of changes in the frequency of an electric muscle signal.

2. A method according to claim 1, wherein the desired area is an area of the lumbar spine.

3. A method according to claim 2, wherein the desired flexion and extension of back muscles are measured as a difference between motions detected by motion sensors placed on an upper part of the lumbar spine and in a sacral area during the entire motion.

4. A method according to claim 1, further comprising a step for rendering flexion values of the back and corresponding electric muscle signals mutually comparable with respect to timing.

5. A method according to claim 2, further comprising a step for rendering flexion values of the back and corresponding electric muscle signals mutually comparable with respect to timing.

6. A method according to claim 3, further comprising a step for rendering flexion values of the back and corresponding electric muscle signals mutually comparable with a respect to timing.

7. A method according to claim 1, wherein the mobility measuring step includes continuously registering movements of the person in the desired area.

8. The method according to claim 1, wherein the mobility measuring step includes simultaneously measuring motion at two areas.

9. The method according to claim 1, wherein the changes in the frequency of the electric muscle signal are determined by a fast Fourier transformation.

10. The method according to claim 1, wherein the mobility measuring step comprises measuring a movement of the person in the desired area.

11. The method according to claim 10, wherein the movement is a movement of a spine of the person.

12. The method according to claim 1, wherein the mobility measuring step includes:

measuring a motion of a sacrum;

measuring a motion of a spine; and calculating a relative motion of the spine with respect to the sacrum by comparing the measured motion of the sacrum with the measured motion of the spine.

13. The method according to claim 1, wherein the electrical activity measuring step includes measuring the electrical activity of the muscles during both flexion and extension.

14. The method according to claim 11, wherein the electrical activity measuring step includes measuring the electrical activity of the muscles during both flexion and extension.

15. The method according to claim 12, wherein the electrical activity measuring step includes measuring the electrical activity of the muscles during both flexion and extension.

16. The method according to claim 11, wherein the evaluating step includes a comparison of a timing of muscle contractions with the movement.

17. The method of claim 16, wherein the evaluating step further comprises an analysis of a relaxation phase signal generated between flexion and extension of the spine.

\* \* \* \* \*